US00PP24914P2

(12) United States Plant Patent
Allen

(10) Patent No.: US PP24,914 P2
(45) Date of Patent: Sep. 23, 2014

(54) ***LEUCANTHEMUM* PLANT NAMED 'SHAPCOTT RUFFLES'**

(50) Latin Name: *Leucanthemum×superbum*
Varietal Denomination: Shapcott Ruffles

(71) Applicant: Anita Allen, South Molton (GB)

(72) Inventor: Anita Allen, South Molton (GB)

( * ) Notice: Subject to any disclaimer, the term of this patent is extended or adjusted under 35 U.S.C. 154(b) by 85 days.

(21) Appl. No.: 13/815,086

(22) Filed: Jan. 30, 2013

(51) Int. Cl.
*A01H 5/00* (2006.01)

(52) U.S. Cl.
USPC ..... Plt./285

(58) Field of Classification Search
USPC ..... Plt./285
See application file for complete search history.

*Primary Examiner* — Anne Grunberg
(74) *Attorney, Agent, or Firm* — Penny J. Aguirre

(57) ABSTRACT

A new cultivar of *Leucanthemum*, 'Shapcott Ruffles', characterized by its capitulums with numerous fine ray florets with variable aspect to the disk portion (outward, reflexed, and curled inward), its cold hardiness to −20° C., its flower stems that stand erect and do not lodge, its height of 45 to 61 cm, its dependably long-lived habit, its use as a long lived cut flower, and its deep green healthy foliage that has been observed to be disease free under the conditions tested.

2 Drawing Sheets

Botanical classification: *Leucanthemum×superbum.*
Variety denomination: 'Shapcott Ruffles'.

CROSS REFERENCE TO RELATED APPLICATIONS

This application is co-pending with a U.S. Plant Patent Application filed for a plant derived from the same breeding program that is entitled *Leucanthemum* Plant Named 'Shapcott Summer Clouds' (U.S. Plant patent application Ser. No. 13/815,089) and *Leucanthemum* Plant Named 'Shapcott Gossamer' (U.S. Plant patent application Ser. No. 13/815,088).

BACKGROUND OF THE INVENTION

The present invention relates to a new and distinct cultivar of *Leucanthemum×superbum* and will be referred to hereafter by its cultivar name, 'Shapcott Ruffles'. 'Shapcott Ruffles' represents a new Shasta daisy grown for landscape use and for use as a cut flower.

The new cultivar of *Leucanthemum* arose from an ongoing controlled breeding project by the Inventor in South Molton, Devon, United Kingdom. The new cultivar derived from crosses made in 1998 between unnamed proprietary plants in the Inventor's breeding program. Seeds were pooled from the crosses and the parents are unknown. The Inventor selected 'Shapcott Ruffles' as a single unique plant amongst the seedlings that resulted from the above crosses in 2001.

Asexual propagation of the new cultivar was first accomplished by division by the Inventor in 2001 in South Molton, Devon, United Kingdom. Asexual propagation by division has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Shapcott Ruffles' as a unique cultivar of *Leucanthemum.*

1. 'Shapcott Ruffles' exhibits capitulums with numerous fine ray florets (1 to 4 mm in width) with variable aspect to the disk portion (outward, reflexed, and curled inward).
2. 'Shapcott Ruffles' reaches a height of 45 to 61 cm (18 to 24 inches).
3. 'Shapcott Ruffles' exhibits cold hardiness to −20° C.
4. 'Shapcott Ruffles' exhibits flower stems that stand erect and do not lodge.
5. 'Shapcott Ruffles' is dependably long-lived.
6. 'Shapcott Ruffles' exhibits deep green foliage.
7. 'Shapcott Ruffles' has been observed to be disease free under the conditions tested.
8. 'Shapcott Ruffles' exhibits flowers that are long lived as a cut flower.

The new *Leucanthemum* can be most closely compared to the cultivars 'H. Seibert' (not patented) and 'Horace Reid' (not patented). They are both similar to 'Shapcott Ruffles' in having capitulums with double ray florets. However, both differ from 'Shapcott Ruffles' in having ray florets that are less numerous and wider, in being a taller in height, and in having stems that tend to lodge without support. 'Shapcott Ruffles' can also be compared to the cultivars from the same breeding program; 'Shapcott Gossamer' and 'Shapcott Summer Clouds'. 'Shapcott Gossamer' differs from 'Shapcott Ruffles' in having capitulums with less ray florets that are narrower and in being taller in height. 'Shapcott Summer Clouds' differs from 'Shapcott Ruffles' in having capitulums with ray florets that are more numerous thinner, and more regular in aspect (all outward).

BRIEF DESCRIPTION OF THE DRAWINGS

The accompanying colored photographs illustrate the overall appearance and distinct characteristics of the new *Leucan-*

*themum*. The photographs were taken of plants about 2 years in age as grown in a garden in South Molton, Devon, United Kingdom.

Figure 1:
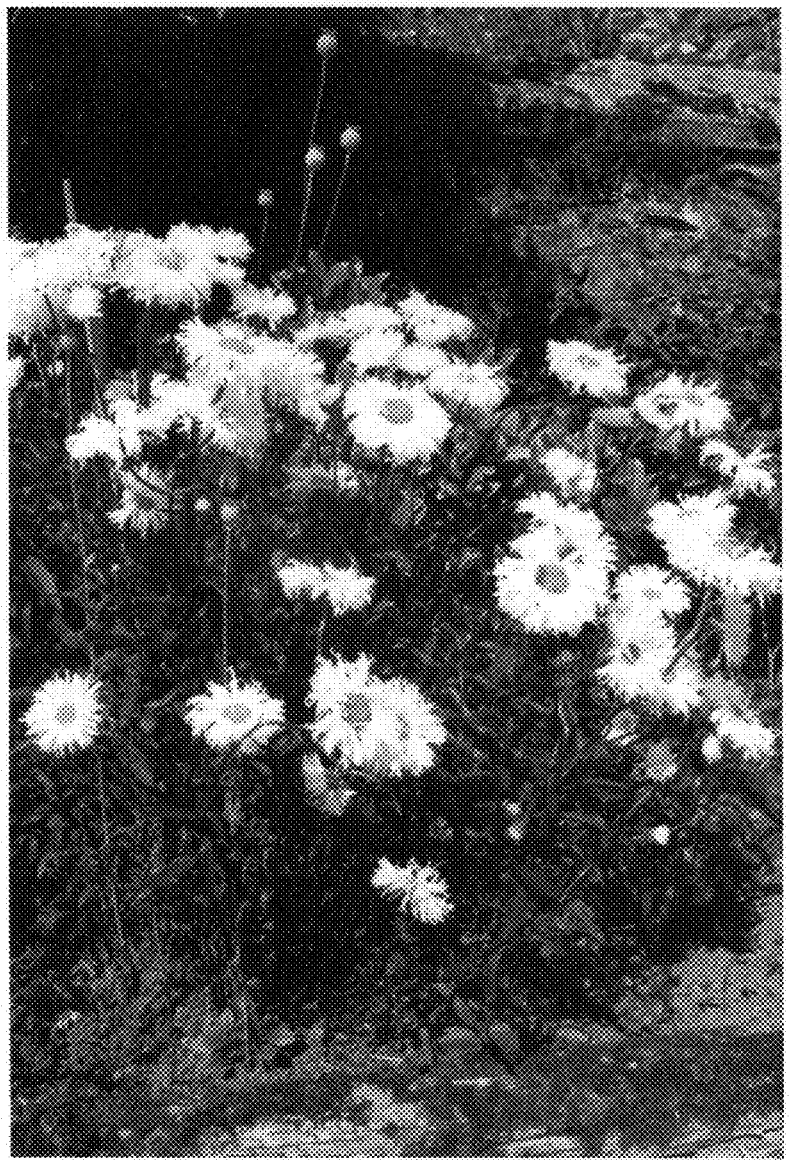

The photograph in FIG. 1 illustrates the plant habit of 'Shapcott Ruffles' in bloom.

Figure 2:
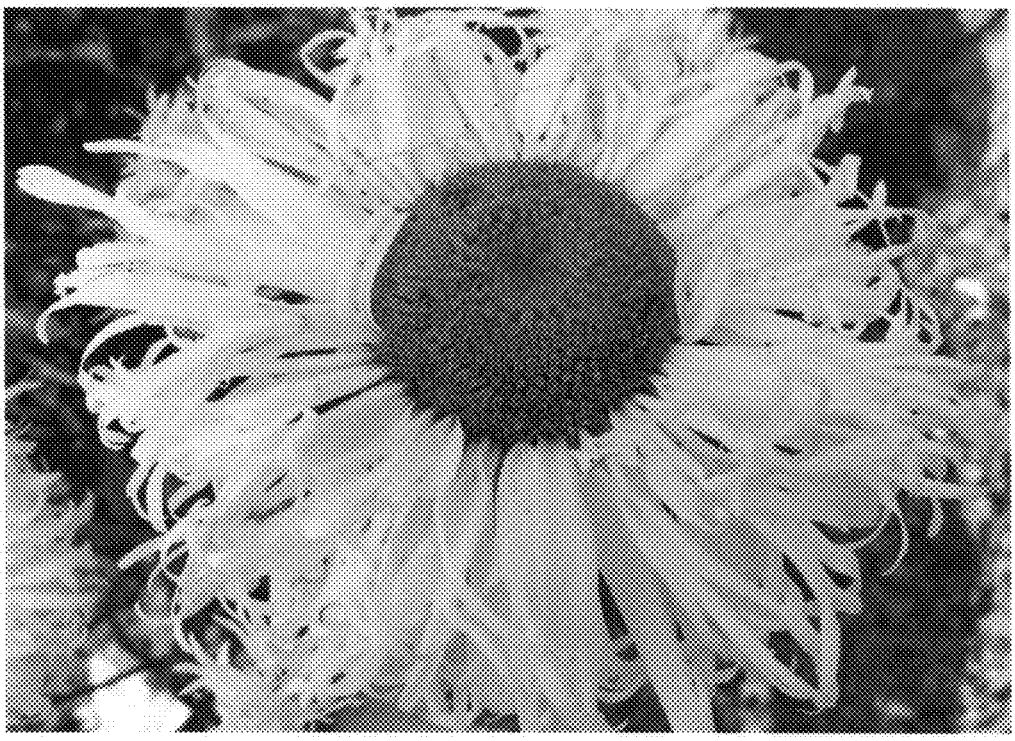

The photograph in FIG. 2 provides a close-up view of the capitulums of 'Shapcott Gossamer'.

Figure 3:
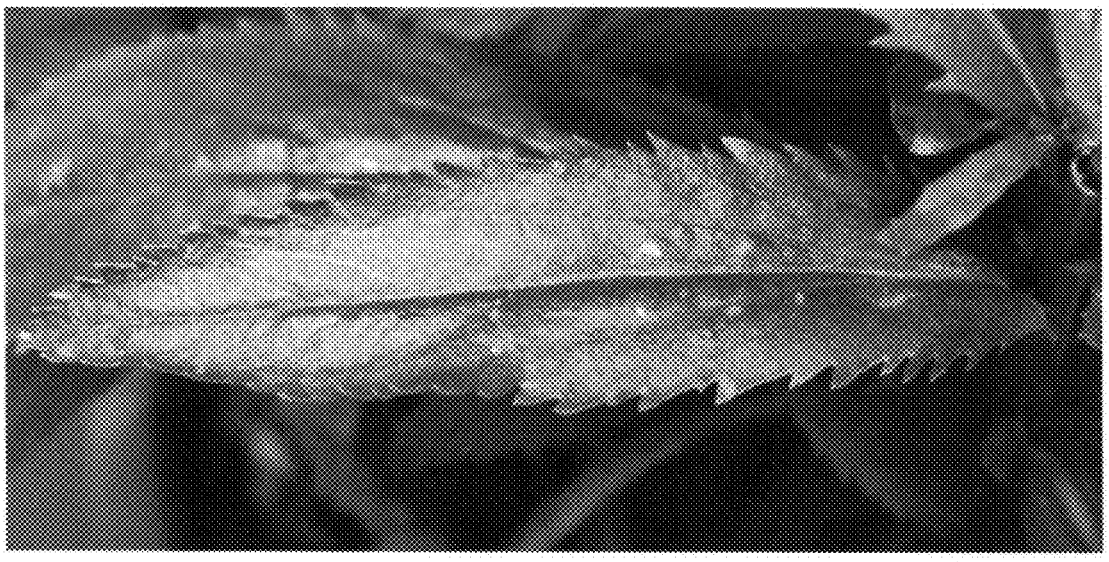

FIG. 3 provides a close-up view of a leaf of 'Shapcott Ruffles'.

The colors in the photographs may differ slightly from the color values cited in the detailed botanical description, which accurately describe the colors of the new *Leucanthemum*.

BOTANICAL DESCRIPTION OF THE PLANT

The following is a detailed description of three month-old plants from a division of the new cultivar as grown outdoors in 5.9-liter containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms for 10 weeks from late June to early August in South Molton, Devon, United Kingdom.

*Plant type*.—Herbaceous perennial, long lived.

*Plant habit*.—Upright, freely branching.

*Height and spread*.—Reaches 45 to 61 cm (18 to 24 inches) and spread.

*Diseases and pests*.—No susceptibility or resistance to diseases or pests has been observed.

*Cold hardiness*.—At least to −20° C.

*Root description*.—Fibrous roots, freely branched, dense.

*Growth rate*.—Vigorous.

*Propagation*.—Division.

Stem description:

*Stem shape*.—Rounded.

*Stem aspect*.—Primarily upright without a tendency to lodge.

*Stem strength*.—Very strong,

*Stem color*.—143B, axial ribs are 166A.

*Stem surface*.—Un-deep axial ribs, moderately glossy, sparsely covered in short strigose hairs average of 0.4 mm in length and 157D in color.

*Lateral branch size*.—Average of 51.2 cm in length and 9 mm in diameter.

*Quantity of lateral branches*.—About 3 lateral stems per main stem.

*Internode length*.—Average of 1.8 cm.

*Branching*.—Moderately free branching.

Foliage description:

*Leaf division*.—Simple.

*Leaf shape*.—Oblanceolate.

*Leaf base*.—Cuneate, short decurrent.

*Leaf apex*.—Broadly acute.

*Leaf margin*.—Serrate.

*Leaf venation*.—Pinnate, upper and lower surfaces 144B to 144C in color.

*Leaf attachment*.—Sessile.

*Leaf arrangement*.—Alternate.

*Leaf surface*.—Upper and lower surfaces; smooth and slightly glossy.

*Leaf color*.—Young foliage; upper surface 137A, lower surface between 143A and 146A, mature foliage; upper surface N137B, lower surface between 137A and N137A.

*Leaf size*.—Average of 11.3 cm in length and 2.9 cm in width.

Inflorescence description:

*Type*.—Capitulum, heterogamous with fine, ligulate ray florets around disk florets in the center, borne on terminals and axillary nodes of lateral branches.

*Capitulum number*.—Average 8 inflorescences lateral stem and 25 per plant.

*Lastingness of inflorescence*.—About 3 weeks.

*Lastingness as a cut flower*.—About 7 days in water without additives.

*Capitulum size*.—Matures to about 4.2 cm in depth and 8.6 cm in diameter, disk size is about 2.7 cm in diameter, receptacle is 4 mm in height and 1.1 cm in diameter.

*Fragrance*.—None detected.

*Involucral bracts*.—About 50 arranged in 3 rows, about 7 mm in length and 2.5 mm in width, ovate in shape, broad acute apex, broad cuneate base, entire margin, smooth and dull on both surfaces, color; upper and lower surface; 143C, margins N199C.

*Buds*.—Flattened globular in shape, an average of 9 mm in length and 1.5 cm in diameter, 144C in color.

*Peduncle*.—Terminal peduncle; 15.7 cm in length, 2.5 mm in diameter, very strong, slightly glossy, smooth, with un-deep axial ribs, 143C to 144B in color and held straight upright, fourth peduncle; 16.6 cm in length, 2.5 mm in diameter, very strong, slightly glossy, smooth, with un-deep axial ribs, 143C to 144B in color and held at an angle of 30°, seventh peduncle; 18.4 cm in length, 2.5 mm in diameter, very strong, slightly glossy, smooth, with un-deep axial ribs, 143C to 144B in color and held at an angle of 30°.

*Ray florets* (*sterile*).—Rotate, Average 60, arranged in multiple rows, cleft parted in shape, aspect is variable; reflexed, outward, and curled inward, about 3.4 cm in length and 1 to 4 mm in width, cleft apex, attenuate base, entire margin, smooth and dull on both surfaces, color: upper side; when opening and fully opened; NN155D, lower surface; when opening and fully opened; NN155D.

*Disk florets* (*bisexual*).—Numerous, about 250, rotate in shape, acute apex, lower 80% fused into a short tube, about 5 mm in length, 1 mm in width at base, 1.5 mm at apex, color: immature; 145A, base 151D, mature apex; 13C, mature mid-section; 145B, mature base; 151C to 151D.

Reproductive organs (present on disk florets only):

*Gynoecium*.—Pistil; 1, 2.5 mm in length, style; 2.5 mm in length and 151D in color, ovary is 151D in color.

*Androcoecium*.—Stamens; 5, fused, form a cylinder around style, 3 mm in length, anther; basifixed and linear in shape, 2 mm in length and 151C in color, pollen; low and 13A in color.

*Fruit/seed*.—None observed.

It is claimed:

1. A new and distinct cultivar of *Leucanthemum* plant named 'Shapcott Ruffles' substantially as herein illustrated and described.

* * * * *